US012558046B2

(12) United States Patent
Takenouchi et al.

(10) Patent No.: US 12,558,046 B2
(45) Date of Patent: Feb. 24, 2026

(54) X-RAY IMAGING APPARATUS AND CONTROL METHOD OF X-RAY IMAGING APPARATUS

(71) Applicant: FUJIFILM Healthcare Corporation, Kashiwa (JP)

(72) Inventors: Shinobu Takenouchi, Chiba (JP); Atsushi Ogawa, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 238 days.

(21) Appl. No.: 18/604,966

(22) Filed: Mar. 14, 2024

(65) Prior Publication Data

US 2024/0315653 A1      Sep. 26, 2024

(30) Foreign Application Priority Data

Mar. 20, 2023      (JP) ................................. 2023-044161

(51) Int. Cl.
*A61B 6/03*          (2006.01)
*A61B 6/00*          (2006.01)

(52) U.S. Cl.
CPC ............ *A61B 6/4464* (2013.01); *A61B 6/487* (2013.01); *A61B 6/547* (2013.01)

(58) Field of Classification Search
CPC .. A61B 6/032; A61B 6/54; A61B 6/04; A61B 6/0487; A61B 6/547; A61B 6/4476; A61B 6/487; A61B 6/545; A61B 6/587; A61B 6/2034; A61B 2090/376; A61B 6/4452; A61B 6/4464; G06T 2207/10072; G06T 2207/10116; G06T 7/70; G06T 3/14
See application file for complete search history.

(56) References Cited

U.S. PATENT DOCUMENTS

2020/0205759 A1*    7/2020   Shirota .................. A61B 6/587

FOREIGN PATENT DOCUMENTS

JP          2012-011057 A       1/2012

* cited by examiner

*Primary Examiner* — Don K Wong
(74) *Attorney, Agent, or Firm* — Paul Teng

(57)          ABSTRACT
Provided is an X-ray imaging apparatus that enables an operator to freely manually move an X-ray source along a rail installed on a ceiling or a floor, and can capture a fluoroscopic image. An X-ray control unit continuously emitting X-rays from an X-ray source and permits fluoroscopy only in a case in which one or more predetermined conditions, including a condition in which the X-ray source is stopped at a predetermined position on a rail corresponding to a position at which an X-ray detector is held, are satisfied. Specifically, the X-ray control unit enables an operation of a fluoroscopy switch, and continuously supplies a tube current and a tube voltage to the X-ray tube in a case in which the operator operates the fluoroscopy switch.

10 Claims, 10 Drawing Sheets

Figures 2A, 2B:
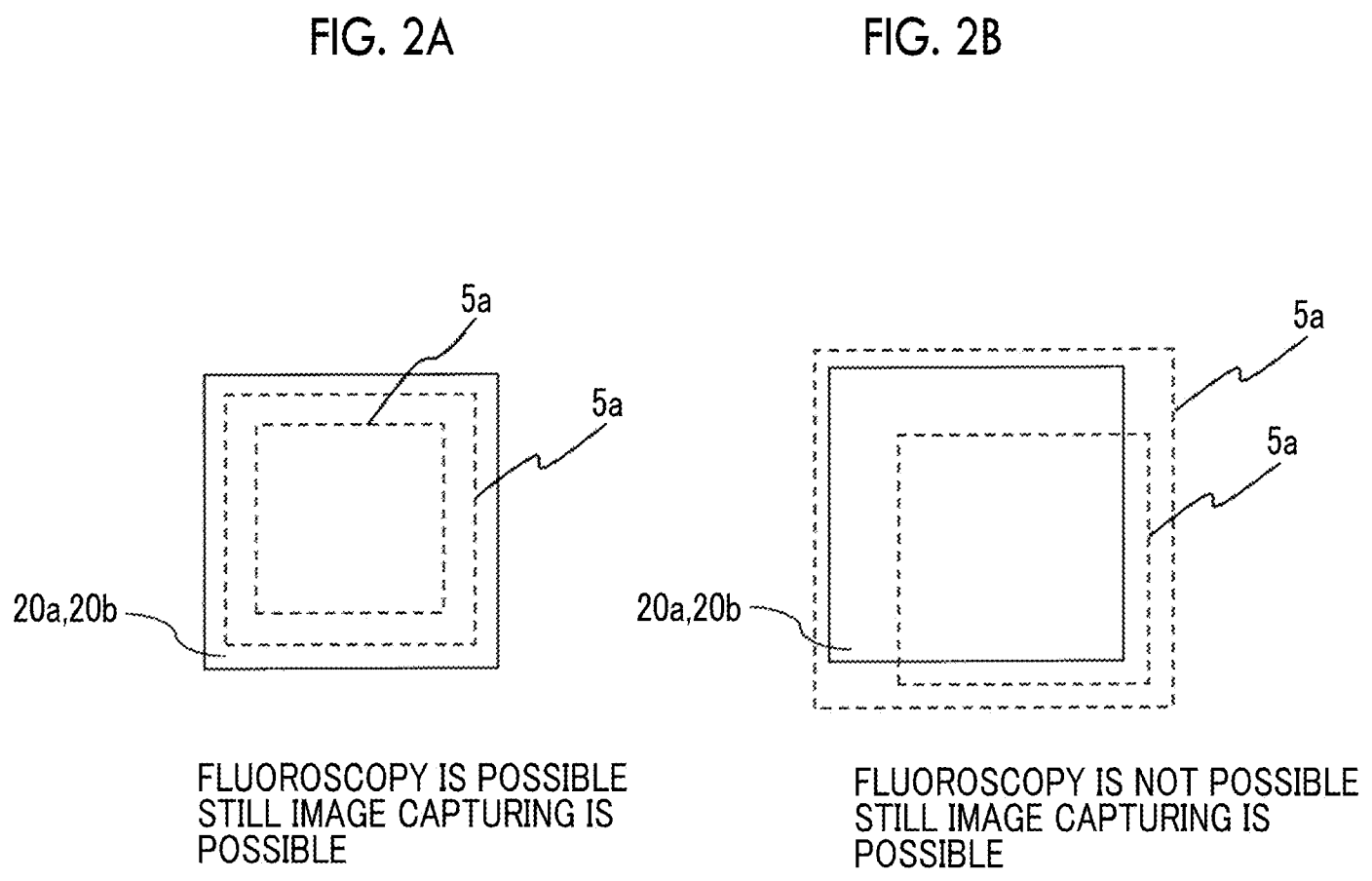

FLUOROSCOPY IS POSSIBLE
STILL IMAGE CAPTURING IS
POSSIBLE

FLUOROSCOPY IS NOT POSSIBLE
STILL IMAGE CAPTURING IS
POSSIBLE

601    CASE OF 17″ × 17″    602

601    CASE OF 14″ × 17″    602

(a)

"ANGLE OF X-RAY SOURCE IS NOT 0° "

F - Ready     R - Ready

49

(b)

F - Ready (FLUOROSCOPY IS POSSIBLE)

F - Ready (FLUOROSCOPY IS NOT POSSIBLE)

R - Ready (STILL IMAGE CAPTURING IS POSSIBLE)

"FLUOROSCOPY IS POSSIBLE"

F - Ready     R - Ready

49

52

F

120

X-RAY IMAGING APPARATUS AND CONTROL METHOD OF X-RAY IMAGING APPARATUS

CROSS-REFERENCE TO RELATED APPLICATION

The present application claims priority from Japanese patent application 2023-044161 filed on Mar. 20, 2023, the content of which is hereby incorporated by reference into this application.

BACKGROUND OF THE INVENTION

1. Field of the Invention

The present invention relates to an X-ray imaging apparatus that performs imaging by moving an X-ray source along a rail disposed on a ceiling or a floor surface and irradiating an imaging target site of a subject in a standing position or recumbent position with X-rays.

2. Description of the Related Art

As an apparatus that irradiates a subject with X-rays for imaging, there are known two types of apparatuses of an X-ray imaging apparatus that captures a still image, such as a chest X-ray imaging apparatus, and an X-ray television (X-ray TV) apparatus (also called as X-ray fluoroscopic apparatus) that captures a moving image (fluoroscopic image) and displays the captured moving image on a display device in real time.

The former X-ray imaging apparatus has a structure in which a rail is installed on a ceiling or a floor, and an X-ray source is moved by an operator along the rail. The subject stands in front of an imaging table for a standing position or lies on an imaging table for a recumbent position. An X-ray detection device, such as a flat panel detector (FPD), is disposed inside the imaging table. Therefore, in the X-ray imaging apparatus, a degree of freedom in disposing the X-ray source is high, and the operator can dispose the X-ray source at a desired position to perform the imaging.

On the other hand, in the latter X-ray TV apparatus, it is it is required by the standard (JIS Z4751-2-54 Medical electrical equipment-Part 2-54: Particular requirements for the basic safety and essential performance of X-ray equipment for radiography and radioscopy) that the X-ray detector is always disposed within an irradiation range of the X-ray source. Therefore, the X-ray source is supported on an upper portion of a bed on which the subject is placed, by a column provided on a side of the bed. A drive mechanism that moves the position of the bed or the X-ray detector and a drive mechanism that moves the position of the X-ray source are controlled to be interlocked, and the X-ray source and the X-ray detector are always disposed to face each other.

JP2012-11057A discloses a technique of detecting whether a cableless FPD cassette is disposed in a vertical orientation or disposed in a horizontal orientation with respect to an imaging table in an X-ray imaging apparatus and displaying the detection result on a console. In this manner, the FPD cassette having an orientation different from that intended by an imaging person is used to prevent re-imaging.

SUMMARY OF THE INVENTION

In recent years, there is a demand to capture the fluoroscopic image by the X-ray imaging apparatus that captures the still image. As described above, in order to capture the fluoroscopic image, it is necessary that the X-ray source and the X-ray detector are always disposed to face each other because the standard described above is satisfied.

However, the X-ray imaging apparatus has a configuration in which the operator can freely manually move the X-ray source along the rail installed on the ceiling or the floor. The operator can also slide a position of the FPD on the imaging table for a recumbent position to a desired position. There are a plurality of types of sizes of the FPD cassette. The operator can also set a height of the FPD of the imaging table for a standing position to a desired height.

That is, in the X-ray imaging apparatus, the position of the X-ray source is not interlocked with the position of the X-ray detector, such as the FPD, the design is made so that the X-ray source can be freely disposed manually, and thus it is not easy to satisfy a condition that the fluoroscopic image is always captured in a relationship in which the X-ray source and the X-ray detector are disposed to face each other.

An object of the present invention is to provide an X-ray imaging apparatus that enables an operator to freely manually move an X-ray source along a rail installed on a ceiling or a floor, and can capture a fluoroscopic image.

In order to achieve the above object, an aspect of the present invention relates to an X-ray imaging apparatus including: a rail installed on a ceiling or a floor surface; an X-ray source; an X-ray source support mechanism unit that supports the X-ray source to be movable along the rail; a steering wheel provided in the X-ray source support mechanism unit; an imaging table for a standing position or for a recumbent position that holds an X-ray detector at an imaging target part of a subject; a still image capturing switch for giving an instruction to capture a still image of the subject; a fluoroscopy switch for giving an instruction to capture a fluoroscopic image of the subject; and an X-ray control unit. In a case in which one or more predetermined conditions are satisfied, the X-ray control unit permits an operation of the fluoroscopy switch. The predetermined conditions include a condition in which the X-ray source that is moved by an operator operating the steering wheel is stopped at a predetermined position on the rail corresponding to a position at which the X-ray detector is held.

According to the aspect of the present invention, it is possible to provide the X-ray imaging apparatus that enables the operator to freely manually move the X-ray source along the rail installed on the ceiling or the floor, and can capture the fluoroscopic image.

BRIEF DESCRIPTION OF THE DRAWINGS

FIG. 1 is a block diagram showing an overall configuration of an X-ray imaging apparatus according to Embodiment 1 of the present invention.

FIGS. 2A and 2B are explanatory diagrams showing a positional relationship between an irradiation field 5a of X-rays of an X-ray imaging apparatus and image reception surfaces 20a and 20b of an X-ray detector according to Embodiment 1.

FIG. 8(*a*) and FIG. 8(*b*) are diagrams showing adjustment of an aperture of a stop 6 of the X-ray imaging apparatus according to Embodiment 1.

FIG. 10(*a*) and FIG. 10(*b*) are explanatory diagrams showing display examples displayed on a monitor 49 in the flow of FIG. 8(*a*) and FIG. 8(*b*).

DESCRIPTION OF THE PREFERRED EMBODIMENTS

Hereinafter, embodiments of the present invention will be described with reference to the accompanying drawings.

Embodiment 1

A configuration of an X-ray imaging apparatus according to Embodiment 1 will be described.

Figure 1:
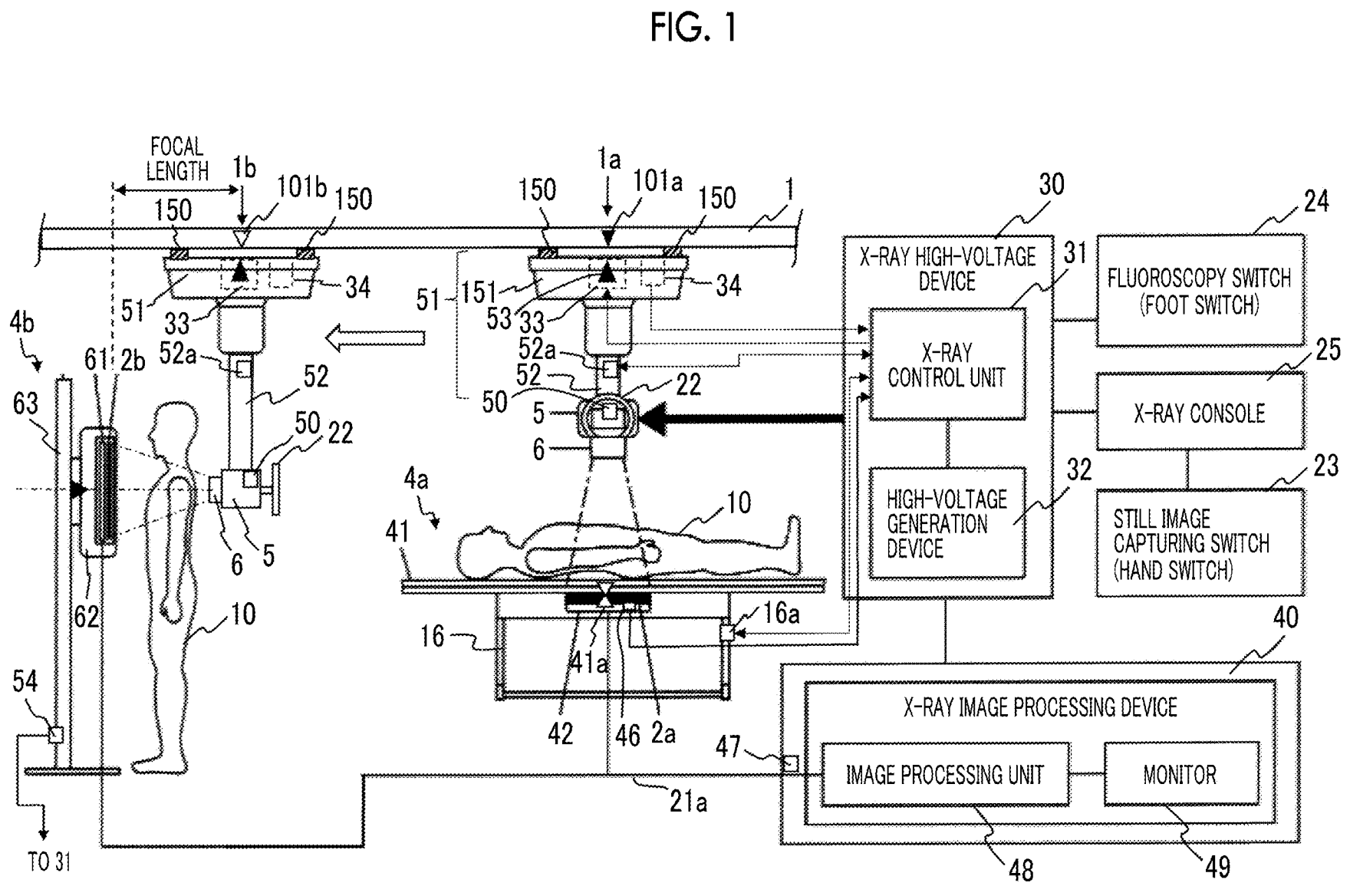
Figure 3:
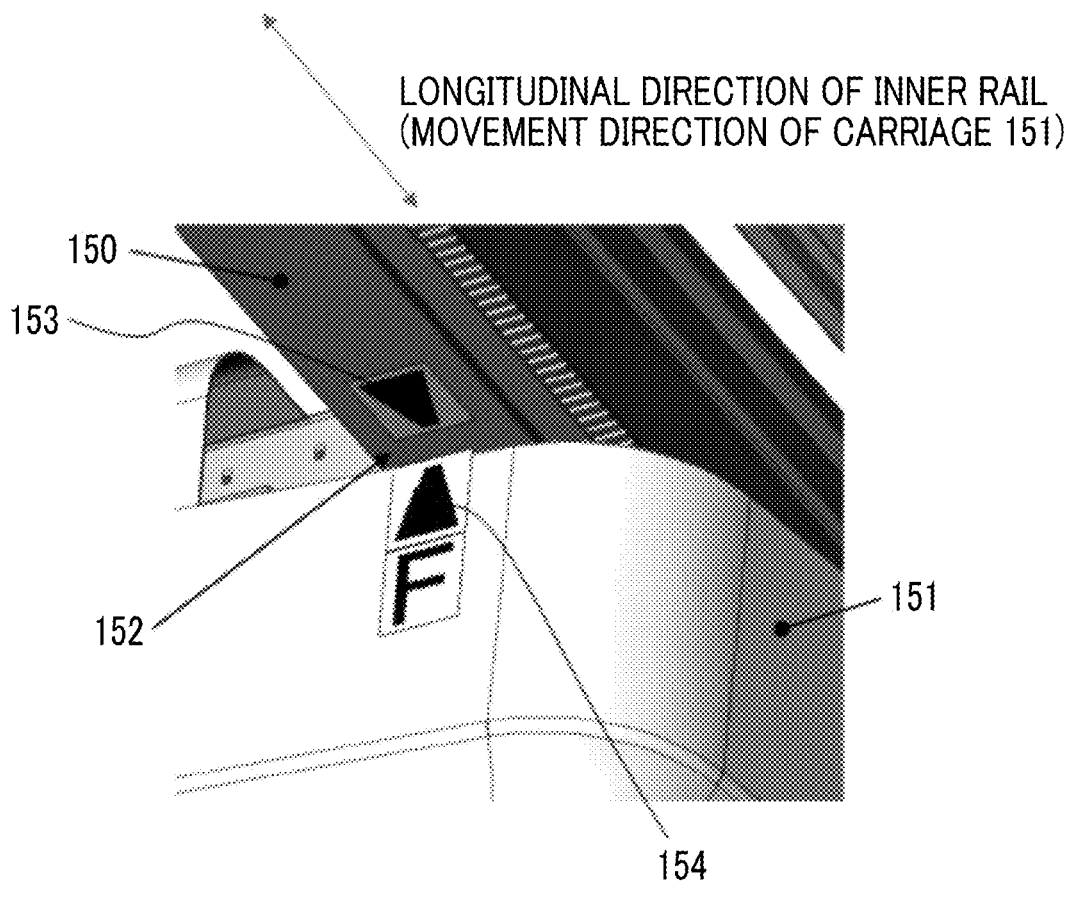
FIG. 3 is a perspective view showing an inner rail 150 of an X-ray source support mechanism unit 51 of the X-ray imaging apparatus according to Embodiment 1.
Figures 4A, 4B:
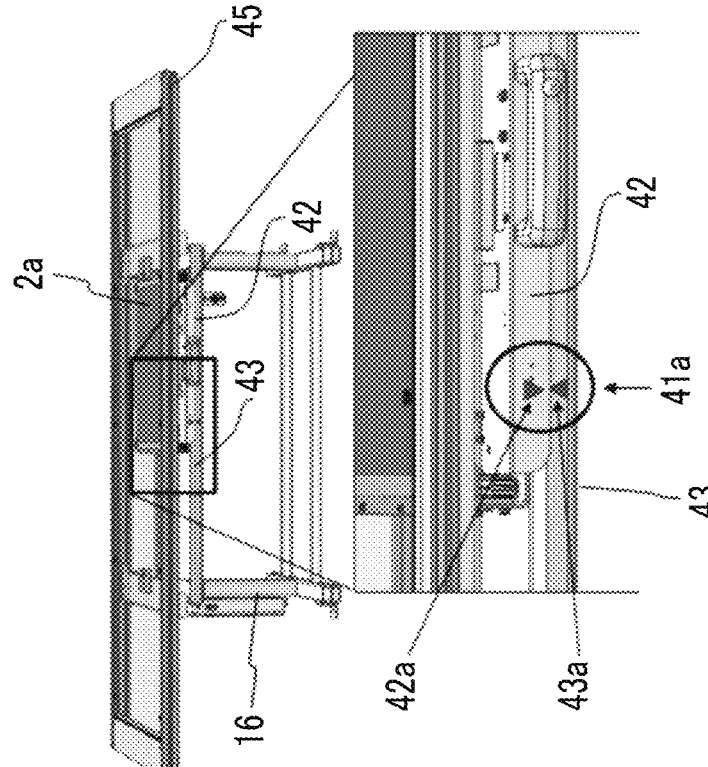
FIGS. 4A and 4B are perspective views showing a structure of an imaging table for a recumbent position in a state in which a top plate 41 of the X-ray imaging apparatus according to Embodiment 1 is removed.

FIG. 1 is a diagram showing an overall configuration of the X-ray imaging apparatus, and FIGS. 2A and 2B are diagrams showing a positional relationship between an irradiation field 5a of X-rays and image reception surfaces 20a and 20b of an X-ray detector. FIG. 3 is a perspective view showing an inner rail 150 of an X-ray source support mechanism unit 51. FIGS. 4A and 4B are perspective views showing a structure of an imaging table for a recumbent position in a state in which a top plate 41 is removed.

The X-ray imaging apparatus comprises a pair of rails 1 installed on a ceiling or a floor surface, an X-ray source 5, and the X-ray source support mechanism unit 51 that supports the X-ray source 5 to be movable along the rails 1. A detailed configuration of the X-ray source support mechanism unit 51 will be described below.

The X-ray source 5 comprises a steering wheel 22. The steering wheel 22 comprises a plurality of operation switches.

In addition, the X-ray imaging apparatus comprises an imaging table for a recumbent position 4a and an imaging table for a standing position 4b. The imaging table for a recumbent position 4a comprises the top plate 41 on which a subject 10 is placed, a frame 45 that supports the top plate 41, a leg part 16 that supports the frame 45 with respect to the floor surface, and a detector holding part 43 that supports an X-ray detector 2a.

The imaging table for a standing position 4b comprises a tray for a standing position 61 that holds an X-ray detector

2b, a detector holding part for a standing position 62 that holds the image reception surface 20b of the X-ray detector 2b to be perpendicular to the floor surface, and a leg part for a standing position 63 that supports the detector holding part for a standing position 62 to be movable up and down with respect to the floor surface.

In addition, the X-ray imaging apparatus comprises a still image capturing switch 23 that receives an instruction to capture a still image of the subject 10, a fluoroscopy switch 24 that receives an instruction to capture a fluoroscopic image of the subject 10, and an X-ray console 25 that receives input of an imaging condition or the like from an operator.

An X-ray high-voltage device 30 that supplies a tube voltage and a tube current is connected to the X-ray source 5. The X-ray high-voltage device 30 includes an X-ray control unit 31, and a high-voltage generation device 32 that generates the tube voltage under the control of the X-ray control unit 31.

An X-ray image processing device 40 is connected to the X-ray detectors 2a and 2b. The X-ray image processing device 40 comprises an image processing unit 48 and a monitor 49. The image processing unit 48 receives output signals of the X-ray detectors 2a and 2b to generate an X-ray image (still image or fluoroscopic image).

A longitudinal direction of the pair of rails 1 matches a longitudinal direction of the top plate 41 of the imaging table for a recumbent position 4a.

The X-ray control unit 31 permits an operation of the fluoroscopy switch 24 only in a case in which predetermined conditions are satisfied.

The conditions in which the X-ray control unit 31 permits the operation of the fluoroscopy switch 24 include a condition in which the X-ray source 5 moved by the operator operating the steering wheel 22 is stopped at a predetermined X-ray source position for fluoroscopy 1a or 1b on the rail 1. The X-ray source position for fluoroscopy 1a or 1b is a position on the rail 1 corresponding to a position at which the X-ray detector 2a of the imaging table for a recumbent position 4a or the X-ray detector 2b of the imaging table for a standing position 4b is held.

Specifically, the X-ray source position for fluoroscopy 1a is a position in the longitudinal direction of the rail 1 for disposing the X-ray source 5 so that the irradiation field 5a of the X-ray source 5 is included in the image reception surface 20a of the X-ray detector 2a of the imaging table for a recumbent position 4a. The X-ray source position for fluoroscopy 1b is a position in the longitudinal direction of the rail 1 for disposing the X-ray source 5 so that the irradiation field 5a of the X-ray source 5 is included in the image reception surface 20b of the X-ray detector 2b of the imaging table for a standing position 4b. That is, since, as shown in FIG. 2A, the positions of the rail 1 in the longitudinal direction for disposing the X-ray source 5 so that the irradiation field 5a of the X-ray source 5 is located inside the image reception surfaces 20a and 20b of the X-ray detectors 2a and 2b, are the X-ray source positions for fluoroscopy 1a and 1b.

More specifically, the X-ray source position for fluoroscopy 1a matches a predetermined tray position for fluoroscopy 41a of the X-ray detector 2a in order to perform fluoroscopy on the imaging table for a recumbent position 4a.

Further, the X-ray source position for fluoroscopy 1b is a position separated from the image reception surface of the X-ray detector 2b held on the imaging table for a standing position 4b by a predetermined distance (focal length of the X-ray source 5) in order to perform fluoroscopy on the imaging table for a standing position 4b.

A configuration of the X-ray source support mechanism unit 51 will be described in detail. The X-ray source support mechanism unit 51 is a mechanism that suspends and supports the X-ray source 5 to be smoothly movable along the rail 1. The X-ray source support mechanism unit 51 comprises a pair of inner rails 150 of which the longitudinal directions are directed in a direction perpendicular to the longitudinal direction of the rail 1, a carriage 151 supported by the inner rails 150, and a column part 52 of which an upper end is fixed to the carriage 151. The carriage 151 is supported to be slidable with respect to the inner rail 150 in the longitudinal direction of the inner rail. The X-ray source 5 is attached to a distal end (lower end) of the column part 52.

Due to such a configuration, the X-ray source support mechanism unit 51 can move the carriage 151 together with the inner rail 150 along the longitudinal direction of the rail 1, and can move the carriage 151 along the longitudinal direction of the inner rail 150. Therefore, the X-ray source 5 supported by the carriage 151 via the column part 52 can be moved in the longitudinal direction of the rail 1, and can be moved in the direction perpendicular to the longitudinal direction of the rail 1.

Further, the column part 52 comprises an expansion and contraction mechanism that can be expanded and contracted in an up-down direction. The expansion and contraction mechanism of the column part 52 will be described in detail below.

In addition, the X-ray source support mechanism unit 51 comprises a brake 33 that stops the movement of the X-ray source 5 along the longitudinal direction of the rail 1 by the control of the X-ray control unit 31, and an X-ray source position detector 34 that detects a position of the X-ray source 5 along the longitudinal direction of the rail 1. The X-ray source position detector 34 detects the position of the X-ray source support mechanism unit 51 for the longitudinal direction of the rail 1. As the X-ray source position detector 34, for example, a potentiometer can be used. The brake 33 may have any structure, but it is preferable to use a static type brake including an electromagnet, such as a brake disclosed in JP2015-167655A.

The output of the X-ray source position detector 34 is input to the X-ray control unit 31. The brake 33 is operated by the control of the X-ray control unit 31 and the operation of the steering wheel 22.

The entire X-ray source support mechanism unit 51 that supports the X-ray source 5 in the longitudinal direction of the rail 1 can be moved by the operator operating the steering wheel 22 to release the brake 33 and holding the steering wheel 22 to move the steering wheel 22 in the longitudinal direction of the rail 1. The X-ray control unit 31 receives the output of the X-ray source position detector 34, determines whether or not the X-ray source support mechanism unit 51 that supports the X-ray source 5 approaches the X-ray source position for fluoroscopy 1a or 1b on the rail 1 by the predetermined distance L, and starts an operation of the brake 33 in a case in which the X-ray source support mechanism unit 51 approaches the X-ray source position for fluoroscopy 1a or 1b by the predetermined distance. The distance L is set to a braking distance of the brake 33 obtained in advance. Accordingly, the X-ray source support mechanism unit 51 is stopped at the X-ray source position for fluoroscopy 1a or 1b on the rail 1 by the braking operation of the brake 33.

As shown in FIG. 1, marks 101a and 101b as marks are attached to the rail 1 at the X-ray source positions for fluoroscopy 1a and 1b. On the other hand, a mark 53 attached to a side surface of a portion of the X-ray source support mechanism unit 51 that is in contact with the rail 1. In a case in which the operator visually checks that the X-ray source support mechanism unit 51 is stopped in a state in which the mark 53 of the X-ray source support mechanism unit 51 matches the mark 101a of the rail 1, the operator can check that the X-ray source 5 is located at the X-ray source position for fluoroscopy 1a for a recumbent position for the longitudinal direction of the rail 1.

In addition, although not shown, the X-ray source support mechanism unit 51 comprises a brake that stops the movement of the X-ray source 5 along the longitudinal direction of the inner rail 150 by the control of the X-ray control unit 31, and an X-ray source position detector that detects a position of the X-ray source 5 along the longitudinal direction of the inner rail 150.

The carriage 151 that suspends the X-ray source 5 in the longitudinal direction of the inner rail 150 can be moved by the operator operating the steering wheel 22 to release the brake of the inner rail 150 and holding the steering wheel 22 to move the steering wheel 22 in the longitudinal direction of the inner rail 150. The X-ray control unit 31 receives the output of an X-ray source position detector that detects the position of the X-ray source 5 in the longitudinal direction of the inner rail 150, determines whether or not the X-ray source 5 approaches a predetermined X-ray source position for fluoroscopy 152 on the inner rail 150 by a predetermined distance L2, and starts an operation of the brake in a case in which the X-ray source 5 approaches the X-ray source position for fluoroscopy 152 by the predetermined distance L2. The distance L2 is set to the braking distance of the brake obtained in advance. Accordingly, the carriage 151 on which the X-ray source 5 is suspended is stopped at the X-ray source position for fluoroscopy 152 on the inner rail 150 by the braking operation of the brake. Accordingly, even in the longitudinal direction of the inner rail 150 (direction perpendicular to the longitudinal direction of the rail 1), the X-ray source 5 can be disposed at a position facing the X-ray detector 2a of the imaging table for a recumbent position 4a. Accordingly, the irradiation field 5a of the X-ray source 5 can be disposed to be located inside the image reception surfaces 20a and 20b of the X-ray detectors 2a and 2b.

The same applies to a case of the imaging table for a standing position 4b. The X-ray source 5 is moved for the longitudinal direction of the rail 1 and is disposed at the X-ray source position for fluoroscopy 1b for a standing position, and then the X-ray source 5 is moved for the longitudinal direction (direction perpendicular to the longitudinal direction of the rail 1) of the inner rail 150 and is disposed at the X-ray source position for fluoroscopy 152 for a standing position, thereby the X-ray source 5 can be disposed at the position facing the X-ray detector 2b of the imaging table for a standing position 4b.

A mark 153 as a mark is attached to the inner rail 150 at the X-ray source position for fluoroscopy 152 as shown in FIG. 3. A mark 154 is attached to a side surface of the carriage 151. Since the mark 153 and the mark 154 match each other, the operator can visually check that the X-ray source 5 is located at the X-ray source position for fluoroscopy 152 for the longitudinal direction of the inner rail 150.

In addition, in a case in which the operator wants to perform imaging other than fluoroscopy, the operator can move the X-ray source support mechanism unit 51, which is stopped at the X-ray source position for fluoroscopy 1a or 1b, to a desired position by the control of the X-ray control unit 31 by manually releasing the brake 33 with the steering wheel 22. Similarly, the inner rail can be moved to a desired position for the longitudinal direction.

The structure of the X-ray source 5 will be described in detail. The X-ray source 5 comprises a housing, an X-ray tube disposed inside the housing, and a stop 6 that limits an irradiation range of X-rays emitted from the X-ray tube. The housing is supported by the lower end of the column part 52 of the X-ray source support mechanism unit 51. The housing comprises a rotation mechanism that rotates the X-ray source 5 and an angle detection unit 50 that detects a rotation angle of the rotation mechanism.

In a case in which the operator operates the steering wheel 22 to rotate the rotation mechanism, a direction in which the X-ray source 5 emits the X-rays can be changed in at least an angle range from a downward direction (0 degrees) to a horizontal direction (90 degrees). In a case in which the direction in which the X-ray source 5 emits the X-rays is the downward direction, the X-rays can be emitted to the subject 10 on the imaging table for a recumbent position 4a to perform imaging. In a case in which the direction in which the X-ray source 5 emits the X-rays is the horizontal direction, the X-rays can be emitted to the subject 10 on the imaging table for a standing position 4b to perform imaging.

The output of the angle detection unit 50 is input to the X-ray control unit 31, and the X-ray control unit 31 can determine whether the imaging in a recumbent position or the imaging in a standing position is performed from the rotation angle of the X-ray source 5.

As described above, the imaging table for a recumbent position 4a comprises the top plate 41 on which the subject 10 is placed, the frame 45 that supports the top plate 41, and the leg part 16 that supports the frame 45 with respect to the floor surface.

The leg part 16 comprises an expansion and contraction mechanism, and supports the frame 45 at a desired height.

The detector holding part 43 is disposed on a lower surface of the frame 45. The detector holding part 43 holds a tray 42 accommodating the X-ray detector 2a. The detector holding part 43 is configured such that the tray 42 can be slid along the longitudinal direction of the top plate 41. For example, the detector holding part 43 is a rail-like member along the longitudinal direction of the top plate 41, and the tray 42 can have a configuration engaging with the detector holding part 43 and being moved in the longitudinal direction of the detector holding part 43.

The detector holding part 43 comprises a tray position sensor 44 that detects whether or not the tray 42 is at the predetermined tray position for fluoroscopy 41a.

For example, as shown in FIG. 4B, the tray position sensor 44 includes a microswitch 44a provided in the detector holding part 43, and the microswitch 44a has a configuration operating in a case of coming into contact with a dog 44b provided in the tray 42 and detecting that the tray 42 is located at the predetermined tray position for fluoroscopy 41a. In addition, the microswitch 44a may be configured to optically detect the dog 44b.

In addition, a configuration may be adopted in which a rail for a microswitch 44c is attached to the detector holding part 43 and the microswitch 44a can be attached at any position along the rail for a microswitch 44c.

The detector holding part 43 comprises a mark 43a indicating the tray position for fluoroscopy 41a. The tray 42 comprises a mark 42a. In a case in which the mark 42a of the tray 42 matches the mark 43a of the detector holding part

43 (FIG. 4A), the operator can visually check that the tray 42 is located at the tray position for fluoroscopy 41a.

The predetermined conditions in which the X-ray control unit 31 permits the operation of the fluoroscopy switch 24 include a condition in which the tray position sensor 44 detects that the tray 42 is located at the predetermined tray position for fluoroscopy 41a on the detector holding part 43. Since this condition is satisfied, the position of the X-ray source 5 stopped at the X-ray source position for fluoroscopy 1a of the rail 1 in the longitudinal direction of the rail 1 matches the center position of the X-ray detector 2a held in a correct orientation by the tray 42 at the tray position for fluoroscopy 41a of the imaging table for a recumbent position 4a.

The tray 42 comprises an orientation detection unit 46 that detects whether or not the X-ray detector 2a is placed in the predetermined correct orientation. A flat panel detector (FPD) having a half-cut size is used here as the X-ray detector 2a. The FPD comprises a connector 21 for outputting a signal which is a detection result of the X-rays, on an end surface of a long side thereof, and a cable 21a is connected to the connector 21.

Figure 5:
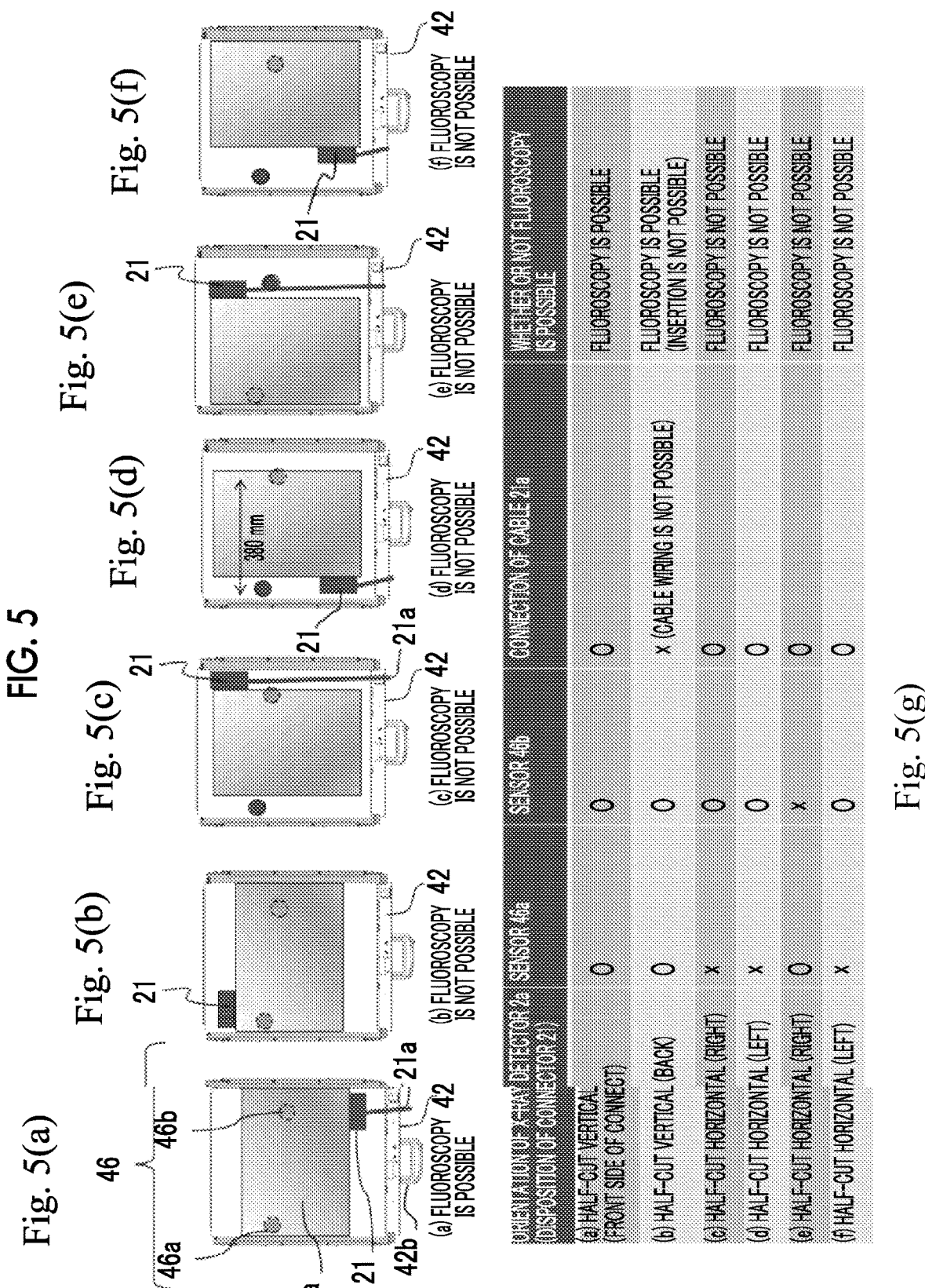
FIG. 5(a) to FIG. 5(f) are top views showing various dispositions of an orientation detection unit 46 and an X-ray detector 2a on a tray 42 of the X-ray imaging apparatus according to Embodiment 1, and FIG. 5(*g*) is an explanatory diagram showing a detection result of the orientation detection unit 46 and whether or not fluoroscopy is possible.

As shown in FIG. 5(a), the orientation detection unit 46 includes two sensors 46a and 46b. The sensors 46a and 46b are disposed, respectively, at predetermined positions on the upper surface of the tray 42, and detect whether or not the X-ray detector 2a is placed on the sensors 46a and 46b. As the sensors 46a and 46b, for example, a photoelectric sensor that detects the presence of the X-ray detector 2a by emitting light to the X-ray detector 2a and receiving the reflected light can be used.

In a case of the X-ray detector 2a having a half-cut size (35.6×43.2 cm), an interval between the sensor 46a and the sensor 46b in a width direction of the tray 42 is set to a distance (for example, 380 mm) longer than the short side and shorter than the long side. The positions of the sensor 46a and the sensor 46b on the tray 42 are determined such that both the sensor 46a and the sensor 46b are covered with the X-ray detector 2a in a case in which the X-ray detector 2a is placed on the tray 42 in a correct disposition, and only one of the sensor 46a or the sensor 46b is covered with the X-ray detector 2a in a case in which the X-ray detector 2a is placed on the tray 42 in an incorrect disposition. It should be noted that, here, the correct disposition is an orientation in which the long side of the X-ray detector 2a having a half-cut size matches the width direction of the tray 42, and the incorrect disposition is an orientation in which the long side of the X-ray detector 2a having a half-cut size is orthogonal to the width direction of the tray 42.

The orientation detection unit 46 further comprises, in addition to the sensors 46a and 46b, a cable connection detection unit 47 that detects whether or not the connector 21 of the X-ray detector 2a is located on the front side (handle 42b side) of the tray 42. The reason why the X-ray detector 2a is placed on the tray 42 so that the connector 21 is located on the front side of the tray 42 is that the cable 21a is pulled out from the tray 42 and is connected to the X-ray image processing device 40. Here, the cable connection detection unit 47 detects whether or not the connector 21 is located on the front side of the tray 42 by detecting whether or not a terminal of the cable 21a is connected to the X-ray image processing device 40. For example, the cable connection detection unit 47 may be a sensor that detects whether or not the terminal of the cable 21a is inserted into an insertion port of the X-ray image processing device 40. Specifically, a microswitch or an optical sensor provided around the insertion port can be used as the cable connection detection unit 47. Additionally, a circuit in which the X-ray image processing device 40 electrically determines whether or not the terminal is inserted into the insertion port of the X-ray image processing device 40 and is electrically connected to the X-ray detector 2a may be disposed in the X-ray image processing device 40, and may be used as the cable connection detection unit 47. In a case in which the X-ray image processing device 40 is also used as the cable connection detection unit 47, and the X-ray image processing device 40 receives the output of the X-ray detector 2a, a configuration may be adopted in which the signal indicating that the terminal of the cable 21a is connected is output to the X-ray control unit 31.

The X-ray control unit 31 permits the operation of the fluoroscopy switch 24 in a case in which the orientation detection unit 46 detects that the X-ray detector 2a is placed on the tray 42 in a predetermined position and orientation.

That is, in a case in which both the sensors 46a and 46b of the orientation detection unit 46 detect that the X-ray detector 2a is placed thereon, and the cable connection detection unit 47 detects that the cable 21a is connected to the X-ray image processing device 40, since the X-ray detector 2a is placed on the tray 42 in the correct orientation as shown in FIG. 5(a), the X-ray control unit 31 permits fluoroscopy (see FIG. 5(g)).

On the other hand, in a case in which, although both the sensors 46a and 46b of the orientation detection unit 46 detect that the X-ray detector 2a is placed thereon, the cable connection detection unit 47 does not detect that the cable 21a is connected to the X-ray image processing device 40, the main body of the X-ray detector 2a is in the correct orientation as shown in FIG. 5(b), but the connector 21 faces the back of the tray 42, and the cable 21a cannot be pulled out from the tray 42, so that the X-ray control unit 31 does not permit fluoroscopy (see FIG. 5(g)).

Further, in a case in which only one of the sensor 46a or 46b of the orientation detection unit 46 detects that the X-ray detector 2a is placed thereon, and the other of the sensor 46a or 46b does not detect the X-ray detector 2a, even in a case in which it is detected that the cable 21a is connected to the X-ray image processing device 40, the orientation of the main body of the X-ray detector 2a is incorrect (long side of the X-ray detector 2a is orthogonal to the width direction of the tray) as shown in FIG. 5(c) to FIG. 5(f), so that the X-ray control unit 31 does not permit fluoroscopy (see FIG. 5(g)).

Next, the expansion and contraction mechanism of the column part 52 that suspends the X-ray source 5 and the expansion and contraction mechanism of the leg part 16 of the imaging table for a recumbent position 4a will be described.

The column part 52 comprises, as the expansion and contraction mechanism that can be expanded and contracted in the up-down direction, a slide rail, a driving unit that drives the slide rail to expand and contract the slide rail, and a displacement sensor 52a that detects the position of the X-ray source 5 by detecting the displacement of the expansion and contraction mechanism. As the displacement sensor 52a, for example, a potentiometer can be used.

On the other hand, the leg part 16 comprises, as the expansion and contraction mechanism that can be expanded and contracted in the up-down direction, a slide rail, a driving unit that drives the slide rail to expand and contract the slide rail, and a displacement sensor 16a that detects the position of the X-ray detector 2a by detecting the displacement of the expansion and contraction mechanism. As the displacement sensor 16a, for example, a potentiometer can be used.

The X-ray control unit 31 can take in the output of the displacement sensor 52a to acquire the position of the X-ray source 5, and operate the driving unit of the column part 52 to dispose the X-ray source 5 at a desired height. Further, the X-ray control unit 31 can take in the output of the displacement sensor 16a to acquire the position of the X-ray detector 2a, and operate the driving unit of the leg part 16 to support the X-ray detector 2a to a desired height.

It is also possible for the operator to manually dispose the X-ray source 5 at a desired position by holding the steering wheel 22 and moving the steering wheel 22 up and down.

Figure 6:
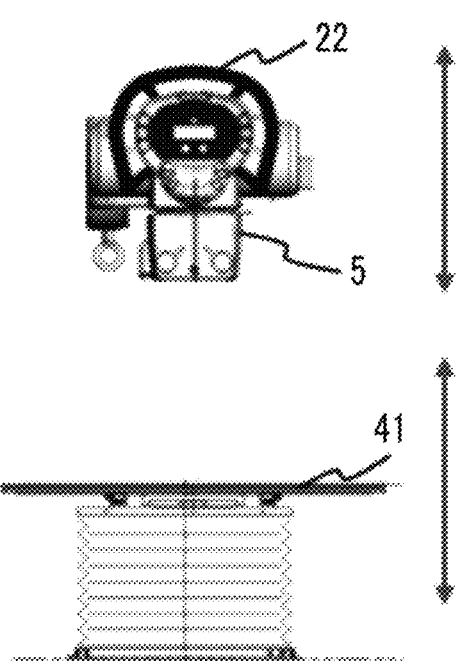
FIG. 6 is an explanatory diagram showing that an X-ray source 5 performs auto tracking of a change in height of an imaging table for a recumbent position 4a of the X-ray imaging apparatus according to Embodiment 1.

In a case in which an auto tracking switch provided in the steering wheel 22 or the X-ray console 25 is turned on, the X-ray control unit 31 obtains the height from the floor surface to the X-ray detector 2a from the output of the displacement sensor 16a of the leg part 16 and further obtains the height of the X-ray source 5 from the output of the displacement sensor 52a of the column part 52 that supports the X-ray source 5, thereby operating the driving unit of the column part 52 so that the focal position of the X-ray source 5 matches the image reception surface of the X-ray detector 2a, to move the X-ray source 5 up and down to follow the displacement of the X-ray detector 2a (see FIG. 6).

Next, the imaging table for a standing position 4b will be described.

As described above, the imaging table for a standing position 4b comprises the tray for a standing position 61 that holds the X-ray detector 2b, the detector holding part for a standing position 62 that holds the image reception surface 20b of the X-ray detector 2b to be perpendicular to the floor surface, and the leg part for a standing position 63 that supports the detector holding part for a standing position 62 to be movable up and down with respect to the floor surface. The leg part for a standing position 63 comprises a slide rail and a driving unit that drives the slide rail to expand and contract the slide rail, and can operate the driving unit to move the detector holding part for a standing position 62 up and down. Accordingly, the X-ray detector 2b can be supported at a height desired by the operator.

In addition, the leg part for a standing position 63 comprises the sensor 54 that detects the height of the detector holding part for a standing position 62. The height of the detector holding part for a standing position 62 detected by the sensor 54 is input to the X-ray control unit 31.

Figure 7:
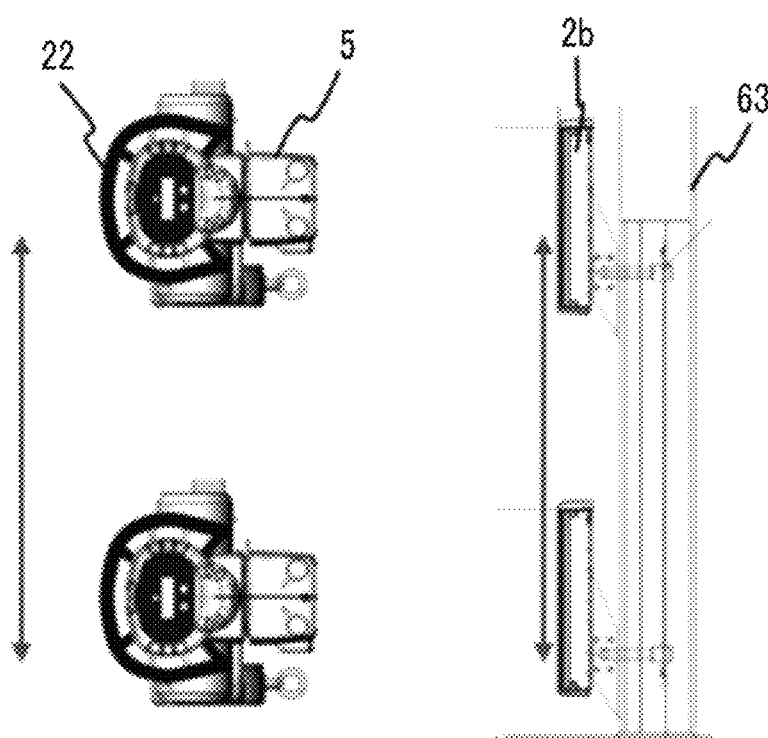
FIG. 7 is an explanatory diagram showing that the X-ray source 5 performs auto tracking of a change in height of an imaging table for a standing position 4b of the X-ray imaging apparatus according to Embodiment 1.

In a case in which the auto tracking switch provided in the steering wheel 22 or the X-ray console 25 is turned on and the X-ray source 5 is rotated by 90 degrees and set to an orientation for the imaging in a standing position, the X-ray control unit 31 obtains the height from the floor surface to the center of the image reception surface of the X-ray detector 2b from the output of the sensor 54, and indicates the driving amount with respect to the driving unit of the column part 52 that supports the X-ray source 5. As a result, the X-ray source 5 can be moved up and down so that the height of the X-ray source 5 matches the center of the image reception surface of the X-ray detector 2a, and the X-ray source 5 can be made to follow the up and down movement of the X-ray detector 2b for a standing position (see FIG. 7).

The predetermined conditions in which the X-ray control unit 31 permits the operation of the fluoroscopy switch 24 include a condition in which a height adjustment unit disposes the X-ray source 5 at a position facing the X-ray detector.

The tray for a standing position 61 has the same configuration as the tray 42 for a recumbent position, and comprises an orientation detection unit that detects whether or not the X-ray detector 2b is placed in a predetermined correct orientation. Since the orientation detection unit of the tray for a standing position 61 includes the two sensors 46a and 46b and has the same configuration as the orientation detection unit 46 of the tray 42 for a recumbent position, the detailed description thereof will be omitted. The orientation detection unit of the tray for a standing position 61 further comprises a cable connection detection unit that detects whether or not the connector 21 of the X-ray detector 2b is located on the front side (handle 42b side) of the tray 42. Since the cable connection detection unit has the same configuration as the cable connection detection unit 47 of the tray 42 for a recumbent position, the description thereof will be omitted.

Figures 8A, 8B:
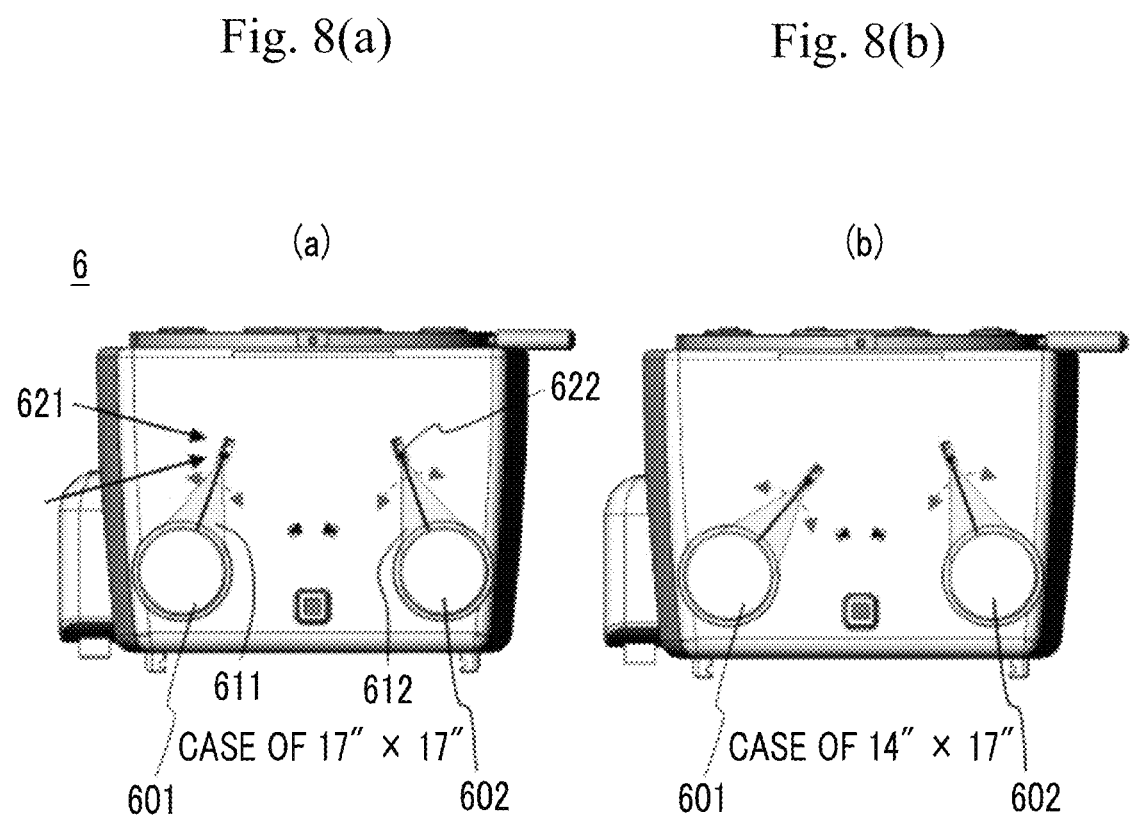

In addition, the stop 6 of the X-ray source 5 comprises adjustment units 601 and 602 for adjusting an aperture (irradiation range) of the stop 6 on the side surface of the housing of the stop 6. The aperture of the irradiation range in the vertical direction is set for the adjustment unit 601, and the aperture of the irradiation range in the horizontal direction is set for the adjustment unit 602. The adjustment units 601 and 602 change the apertures in a case in which the operator rotates the adjustment units 601 and 602. The adjustment units 601 and 602 comprise triangular indicator plates 611 and 612. On the side surface of the housing of the stop 6, gradations 621 and 622 indicating the apertures (maximum apertures during fluoroscopy) in which the irradiation range of the stop 6 matches the image reception surfaces 20a and 20b of the X-ray detectors 2a and 2b are drawn in advance in accordance with the sizes of the X-ray detectors 2a and 2b. FIG. 8(a) shows the gradations 621 and 622 indicating the apertures (maximum apertures during fluoroscopy) matching the image reception surfaces 20a and 20b in a case in which the X-ray detectors 2a and 2b have a size of 17 inches×17 inches, FIG. 8(b) shows the gradations 621 and 622 indicating the apertures (maximum apertures during fluoroscopy) matching the image reception surfaces 20a and 20b in a case in which the X-ray detectors 2a and 2b have a size of 14 inches×17 inches.

In a case in which the operator rotates the adjustment units 601 and 602 so that distal ends of the triangular indicator plates 611 and 612 are directed toward desired positions within a range of inside the gradations 621 and 622 (close to the center of the housing of the stop 6), so that a desired aperture can be set for the stop 6.

Control Operation of X-Ray Control Unit 31 During Fluoroscopy

Figure 9:
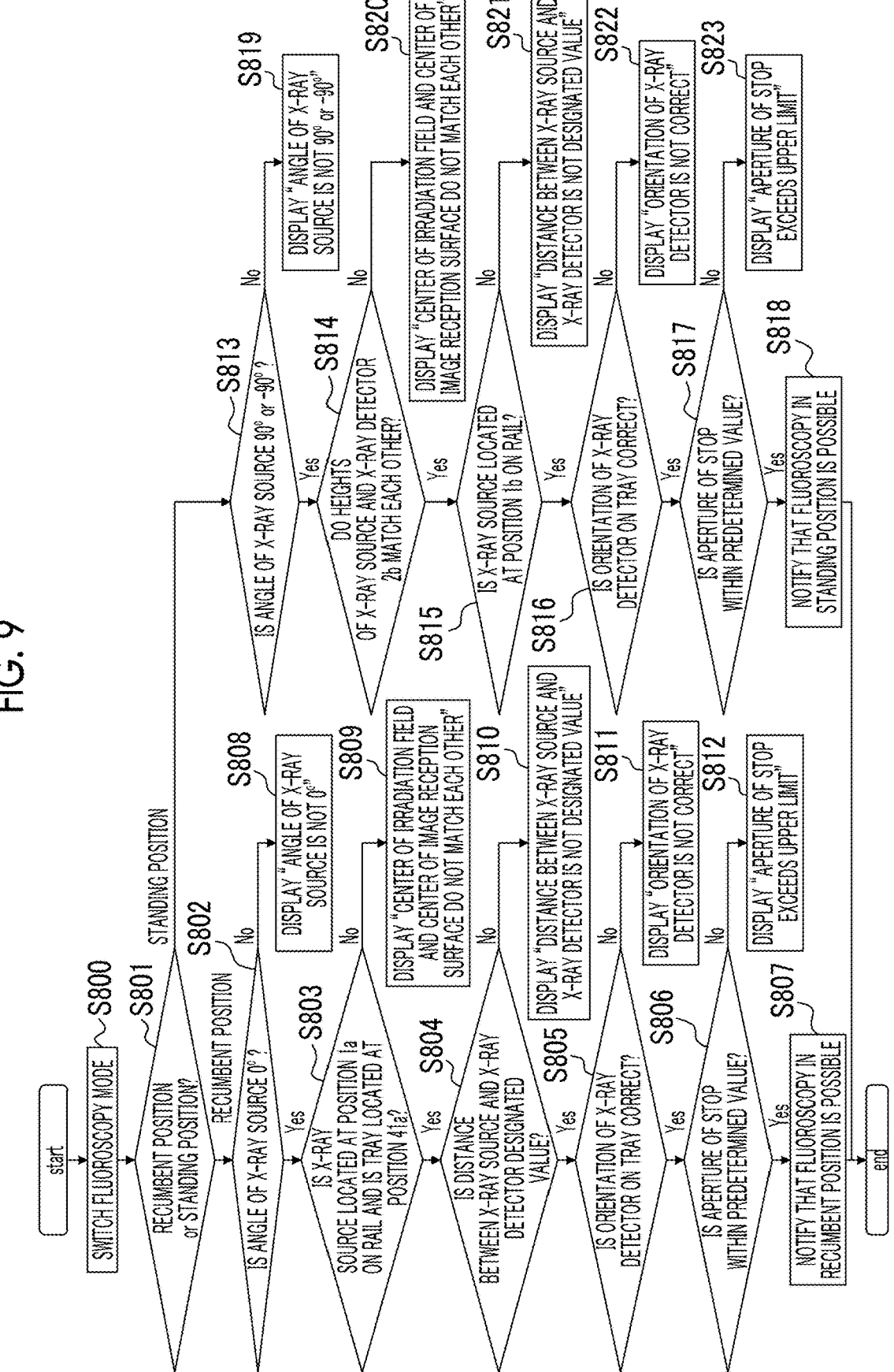
FIG. 9 is a flowchart showing an operation of an X-ray control unit 31 of the X-ray imaging apparatus according to Embodiment 1.

Next, in a case in which fluoroscopy is performed using the X-ray imaging apparatus according to the present embodiment, the X-ray control unit 31 operates as in the flowchart of FIG. 9.

The X-ray control unit 31 is composed of a computer or the like comprising a processor such as a central processing unit (CPU) or a graphics processing unit (GPU) and a memory, and the CPU reads and executes a program stored in the memory, so that the operation of the flow of FIG. 9 is realized by software. It should be noted that the X-ray control unit 31 may be partially or entirely configured with hardware. For example, a circuit need only be designed to realize the function of each unit by using a custom IC such as an application specific integrated circuit (ASIC) or a programmable IC such as a field-programmable gate array (FPGA).

Steps S800 and S801

In a case in which it is detected that the operator operates the steering wheel 22 or the X-ray console 25 to switch a mode to a fluoroscopic mode (step S800), the X-ray control unit 31 takes in the output of the angle detection unit 50 and determines an orientation of the X-ray source 5. In a case in which the angle of the X-ray source 5 is directed in the downward orientation, it is determined that the imaging in a recumbent position is performed, and the process proceeds to step S802. In a case in which the angle of the X-ray source 5 is horizontal, it is determined that the imaging in a standing position is performed, and the process proceeds to step S813. It should be noted that the determination may be performed by the operator inputting whether the recumbent position or the standing position by the operation of the X-ray console 25 or the like and the X-ray control unit 31 receiving the input.

Steps S802 and S808

Figures 10A, 10B, 11:
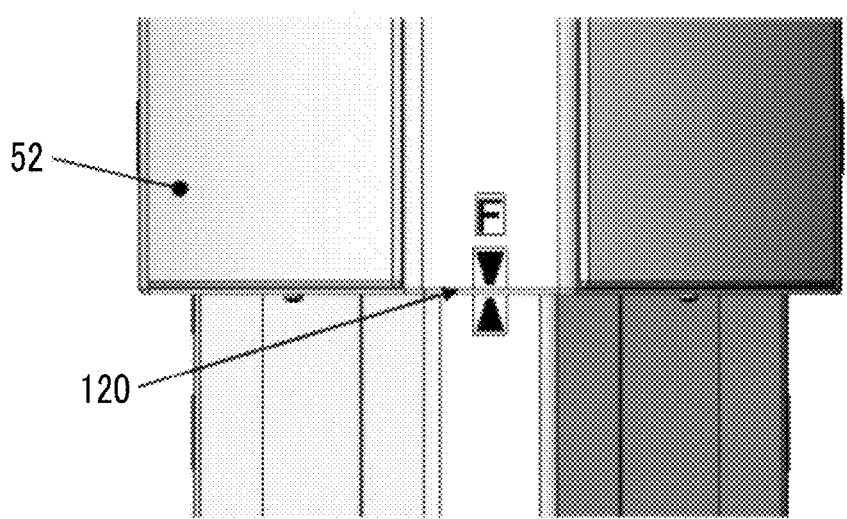
FIG. 11 is a diagram showing a position of a column part 52 in a case in which a height of the X-ray source 5 is manually set in the X-ray imaging apparatus according to Embodiment 1.

In a case of the imaging in a recumbent position, the X-ray control unit 31 further determines whether or not the angle of the X-ray source 5 is 0° (downward orientation) from the output of the angle detection unit 50. In a case in which the angle is not 0°, the irradiation field 5a of the X-ray source 5 is not included inside the image reception surface 20a of the X-ray detector 2a of the imaging table for a recumbent position 4a. Therefore, the X-ray control unit 31 proceeds to step S808, and displays error display on the monitor 49 of the X-ray image processing device 40. Specifically, for example, as shown in FIG. 10(a), in step S808, the X-ray control unit 31 displays "The angle of the X-ray source is not 0°" on the monitor 49.

In a case in which the angle of the X-ray source 5 is 0° in step S802, the X-ray control unit 31 proceeds to step S803.

Steps S803 and S809

In step S803, the X-ray control unit 31 takes in the output of the X-ray source position detector 34 to determine whether or not the X-ray source 5 is stopped at the X-ray source position for fluoroscopy 1a or 152 for the longitudinal direction of the rail 1 and the longitudinal direction of the inner rail 150.

Further, the X-ray control unit 31 takes in the output of the tray position sensor 44 and determines whether or not the tray 42 is located at the tray position for fluoroscopy 41a.

In a case in which the X-ray source 5 is not stopped at the X-ray source position for fluoroscopy 1a or 152 or the tray 42 is not located at the tray position for fluoroscopy 41a, the process proceeds to step S809, and the error display is displayed on the monitor 49 of the X-ray image processing device 40. Specifically, in step S809, the X-ray control unit 31 displays "The center of the irradiation field does not match the center of the image reception surface" on the monitor 49.

In a case in which the X-ray source 5 is stopped at the X-ray source position for fluoroscopy 1a and the tray 42 is located at the tray position for fluoroscopy 41a, the X-ray control unit 31 proceeds to step S804.

Steps S804 and S810

In step S804, the X-ray control unit 31 determines whether or not the auto tracking switch provided in the steering wheel 22 or the X-ray console 25 is turned on.

In a case in which the auto tracking switch is not turned on, the process proceeds to step S810, and the error display is displayed on the monitor 49 of the X-ray image processing device 40. Specifically, in step S810, the X-ray control unit 31 displays "The distance between the X-ray source and the X-ray detector is not a designated value" on the monitor 49.

In a case in which the auto tracking switch is turned on, the X-ray control unit 31 proceeds to step S805.

Steps S805 and S811

In step S805, the X-ray control unit 31 takes in the detection result of the orientation detection unit 46 to determine the orientation of the X-ray detector 2a on the tray 42.

In a case in which the X-ray detector 2a is not placed on the tray 42 in the correct orientation, the process proceeds to step S811, and the error display is displayed on the monitor 49 of the X-ray image processing device 40. Specifically, in step S811, the X-ray control unit 31 displays "The orientation of the X-ray detector is incorrect" on the monitor 49.

In a case in which the X-ray detector 2a is placed on the tray 42 in the correct orientation, the X-ray control unit 31 proceeds to step S806.

Steps S806 and S812

In step S806, the X-ray control unit 31 takes in the aperture set in the adjustment unit of the stop 6 of the X-ray source 5 of the steering wheel 22, and determines whether or not the maximum value is equal to or less than a predetermined value which is predetermined in accordance with the size of the X-ray detector 2a. In a case in which the aperture of the stop 6 is larger than the aperture (maximum aperture during fluoroscopy) that matches the image reception surfaces 20a and 20b, the process proceeds to step S812, and the error display is displayed on the monitor 49 of the X-ray image processing device 40. Specifically, in step S811, the X-ray control unit 31 displays "The aperture of the stop exceeds the upper limit" on the monitor 49.

In a case in which the aperture of the stop is equal to or less than the predetermined value which is predetermined in accordance with the X-ray detector 2a, the X-ray control unit 31 proceeds to step S807.

Step S807

Since all the conditions determined in steps S802 to S806 as described above are satisfied, the X-ray control unit 31 displays display for notifying the operator that the fluoroscopy in a recumbent position is possible on the monitor 49, for example, as in FIG. 10(b), and permits the operation of the fluoroscopy switch 24. In a case in which the fluoroscopy switch 24 is stepped on (operated), the operation is received, and the X-ray control unit 31 continuously supplies the tube current and the tube voltage for fluoroscopy to the X-ray source 5 from the high-voltage generation device 32.

Consequently, the X-rays are continuously emitted from the X-ray source 5. As shown in FIG. 2A, the irradiation field 5a of the X-rays is located inside the image reception surface 20a of the X-ray detector 2a. Therefore, it is possible to detect the X-rays passing through the subject 10 by using the X-ray detector 2a while avoiding invalid exposure to the subject 10. The signals detected by the X-ray detector 2a are input to the X-ray image processing device 40 via the cable 21a.

The image processing unit 48 of the X-ray image processing device 40 generates an X-ray image (moving image) from the received signals, and displays the X-ray image on the monitor 49.

Accordingly, usually, the X-ray imaging apparatus is the X-ray imaging apparatus that captures the still image by disposing the X-ray detector 2a and the X-ray source 5 at positions desired by the operator and operating the still image capturing switch 23 via the operator, and can capture the fluoroscopic image only in a case in which the conditions of steps S802 to S806 are satisfied.

On the other hand, in a case in which the X-ray control unit 31 determines that the imaging in a standing position is performed in step S801, the X-ray control unit 31 proceeds to step S813 and performs control as follows.

Steps S813 and S819

In a case of the imaging in a standing position, the X-ray control unit 31 first takes in the output of the angle detection unit 50 to determine the orientation of the X-ray source 5. In a case in which the angle of the X-ray source 5 is not 900 or −90° (horizontal orientation), the irradiation field 5a of the X-ray source 5 is not included inside the image reception surface 20b of the X-ray detector 2a of the imaging table for a standing position 4b. Therefore, the X-ray control unit 31 proceeds to step S819, and displays error display on the monitor 49 of the X-ray image processing device 40. Specifically, in step S819, the X-ray control unit 31 displays "The angle of the X-ray source is not 900 or −90°'" on the monitor 49.

In a case in which the angle of the X-ray source 5 is 0° in step S813, the X-ray control unit 31 proceeds to step S814.

Steps S814 and S820

In step S814, the X-ray control unit 31 determines whether or not the auto tracking switch provided in the steering wheel 22 or the X-ray console 25 is turned on. In a case in which the auto tracking switch is not turned on, the process proceeds to step S820, and the error display is displayed on the monitor 49 of the X-ray image processing device 40. Specifically, in step S820, the X-ray control unit 31 displays "The center of the irradiation field does not match the center of the image reception surface" on the monitor 49.

In a case in which the auto tracking switch is turned on, the X-ray control unit 31 proceeds to step S815.

Steps S815 and S821

In step S815, the X-ray control unit 31 takes in the output of the X-ray source position detector 34 to determine whether or not the X-ray source 5 is stopped at the X-ray source position for fluoroscopy 1b for the longitudinal direction of the rail 1 and the X-ray source 5 is stopped at the X-ray source position for fluoroscopy 152 for the longitudinal direction of the rail 1 and the longitudinal direction of the inner rail 150.

In a case in which the X-ray source 5 is not stopped at the X-ray source position for fluoroscopy 1b or 152, the process proceeds to step S821, and the error display is displayed on the monitor 49 of the X-ray image processing device 40. Specifically, in step S821, the X-ray control unit 31 displays "The distance between the X-ray source and the X-ray detector is not a designated value" on the monitor 49.

In a case in which the X-ray source 5 is stopped at the X-ray source position for fluoroscopy 1b or 152, the X-ray control unit 31 proceeds to step S816.

Steps S816 and S822

In step S816, the X-ray control unit 31 takes in the detection result of the orientation detection unit of the tray for a standing position 61 to determine the orientation of the X-ray detector 2b on the tray for a standing position 61. In a case in which the X-ray detector 2b is not placed on the tray for a standing position 61 in the correct orientation, the process proceeds to step S822, and the error display is displayed on the monitor 49 of the X-ray image processing device 40. Specifically, in step S811, the X-ray control unit 31 displays "The orientation of the X-ray detector is incorrect" on the monitor 49.

In a case in which the X-ray detector 2b is placed on the tray for a standing position 61 in the correct orientation, the X-ray control unit 31 proceeds to step S817.

Steps S817 and S823

In step S817, the X-ray control unit 31 takes in the aperture set in the adjustment unit of the stop 6 of the X-ray source 5 of the steering wheel 22, and determines whether or not the maximum value is equal to or less than a predetermined value which is predetermined in accordance with the size of the X-ray detector 2*b*. In a case in which the aperture is larger than the predetermined value, the process proceeds to step S823, and the error display is displayed on the monitor 49 of the X-ray image processing device 40. Specifically, in step S811, the X-ray control unit 31 displays "The aperture of the stop exceeds the upper limit" on the monitor 49.

In a case in which the aperture of the stop is equal to or less than the predetermined value which is predetermined in accordance with the size of the X-ray detector 2*b*, the X-ray control unit 31 proceeds to step S818.

Step S818

Since all the conditions determined in steps S813 to S817 as described above are satisfied, the X-ray control unit 31 displays display for notifying the operator that the fluoroscopy in a standing position is possible on the monitor 49, and permits the operation of the fluoroscopy switch 24. In a case in which the fluoroscopy switch 24 is stepped on (operated), the operation is received, and the X-ray control unit 31 continuously supplies the tube current and the tube voltage for fluoroscopy to the X-ray source 5 from the high-voltage generation device 32.

Consequently, the X-rays are continuously emitted from the X-ray source 5. As shown in FIG. 2A, the irradiation field 5*a* of the X-rays is located inside the image reception surface 20*b* of the X-ray detector 2*b*. Therefore, it is possible to perform fluoroscopy of the subject 10 in a standing position by using the X-ray detector 2*b* while avoiding invalid exposure to the subject 10.

Control Operation of X-Ray Control Unit 31 During Still Image Capturing

The operator operates the steering wheel 22 and the X-ray console 25 to dispose the X-ray source 5 at a desired position with respect to the X-ray detectors 2*a* and 2*b* in either a recumbent position or a standing position. That is, the present invention is not limited to a case in which the irradiation field 5*a* of the X-rays is included inside the image reception surfaces 20*a* and 20*b* of the X-ray detectors 2*a* and 2*b* as shown in FIG. 2A, and a part of the irradiation field 5*a* of X-rays may be located outside the image reception surfaces 20*a* and 20*b* as shown in FIG. 2B. In a case in which the operator operates the still image capturing switch 23, the X-ray control unit 31 receives the operation and supplies the tube current and the tube voltage for still image capturing from the high-voltage generation device 32 to the X-ray source 5.

Accordingly, the X-rays are emitted from the X-ray source 5, and the X-rays passing through the subject 10 are detected by the X-ray detector 2*a* or 2*b*. The signals detected by the X-ray detector 2*a* are input to the X-ray image processing device 40 via the cable 21*a*. The image processing unit 48 of the X-ray image processing device 40 generates an X-ray image (still image) from the received signals, and displays the X-ray image on the monitor 49.

As described above, the X-ray imaging apparatus according to Embodiment 1 is an X-ray imaging apparatus that enables the operator to freely manually move the X-ray source along the rail 1 installed on the ceiling, and can capture the fluoroscopic image even in a case of the recumbent position and the standing position in a case in which a plurality of the predetermined conditions are satisfied, so that the X-ray imaging apparatus is convenient.

It should be noted that, in the present embodiment, the configuration is adopted in which the error display is performed in step S810 in a case in which the auto tracking switch is not turned on in step S804, but the X-ray source 5 may be disposed at a predetermined position from the X-ray detector 2*a* by manually moving the X-ray source 5 up and down and setting the expansion and contraction mechanism of the column part 52 at a predetermined height 120 as shown in FIG. 11. However, the leg part 16 of the imaging table for a recumbent position 4*a* is limited to a case in which the expansion and contraction mechanism is not provided or the expansion and contraction mechanism is set not to operate.

Embodiment 2

Figure 12:
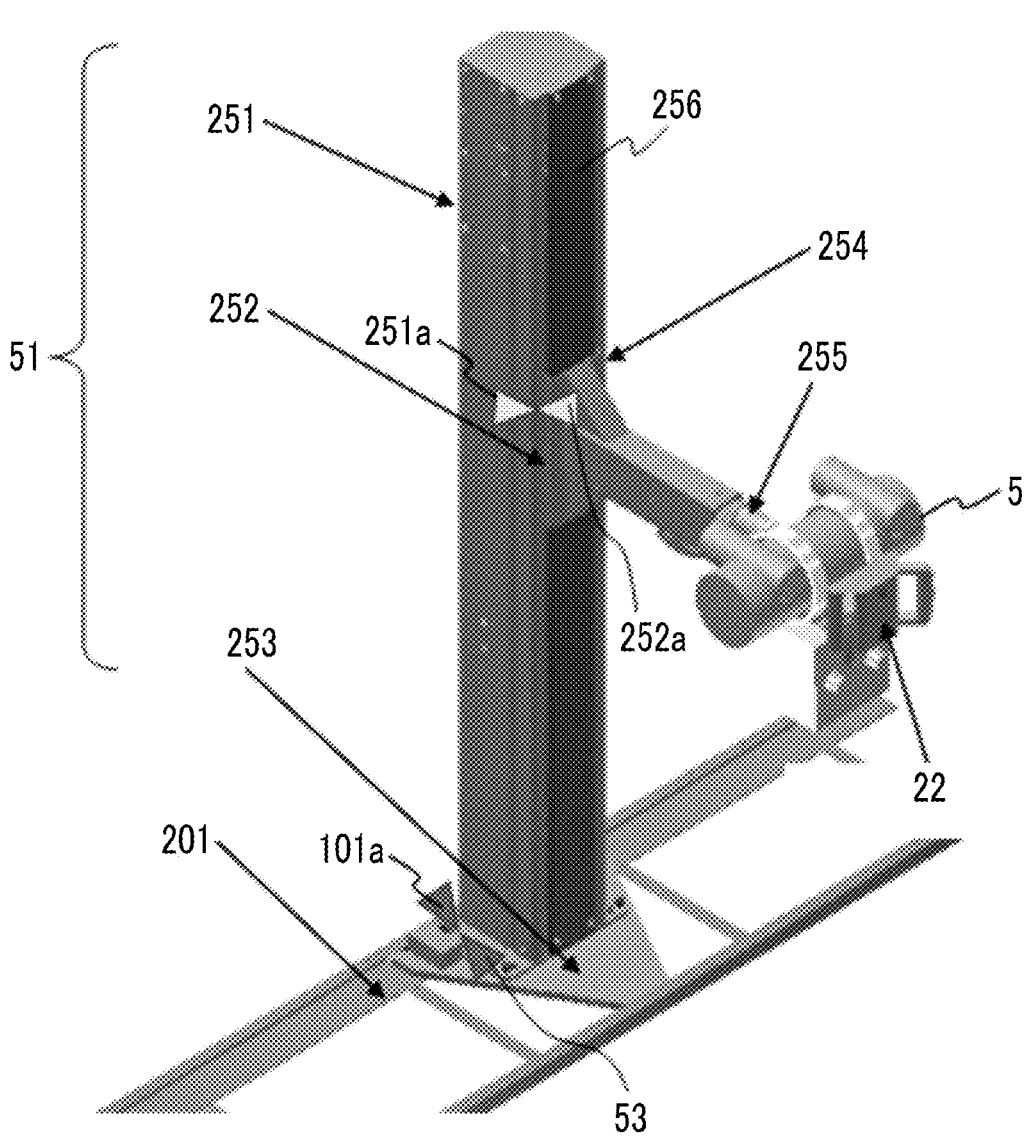
FIG. 12 is a perspective view showing a structure of an X-ray source support mechanism unit 51 of an X-ray imaging apparatus according to Embodiment 2.

Although the X-ray imaging apparatus according to Embodiment 1 has a structure in which the rail 1 is installed on the ceiling, the X-ray imaging apparatus according to Embodiment 2 has a structure in which a rail 201 is set on the floor surface as shown in FIG. 12.

The X-ray source support mechanism unit 51 includes a base 253 that is fitted to the rail 201 and that is slidable along the rail 201, and a column 251 that is erected on the base 253. The column 251 is provided with a guide groove 256 in the up-down direction, and one end of the arm 252 is fitted to the guide groove 256 to be movable up and down. The X-ray source 5 is attached to the distal end of the arm 252 via a joint 255. The joint 255 rotatably holds the X-ray source 5 at the distal end of the arm 252. Accordingly, the angle of the X-ray source 5 can be rotated at least in a range of 0° (downward orientation) for the imaging in a recumbent position to 90° (horizontal orientation) for the imaging in a standing position.

The arm 252 can be moved up and down along the guide groove 256 by a built-in driving unit. The driving unit is controlled by the X-ray control unit 31. Accordingly, it is possible to perform the auto tracking of moving the X-ray source 5 up and down so that the distance between the X-ray source 5 and the X-ray detector 2*a* of the imaging table for a recumbent position 4*a* is maintained at the predetermined distance. In addition, it is also possible to perform the auto tracking for matching the heights of the X-ray source 5 and the X-ray detector 2*b* of the imaging table for a standing position 4*b* with each other.

The arm 252 can also be manually moved up and down along the guide groove 256. In this case, by manually moving the arm 252 in the up-down direction so that a mark 251*a* provided at a predetermined height of the column 251 and a mark 252*a* provided at the base of the arm 252 match each other, the X-ray source 5 can be disposed at a predetermined distance with respect to the X-ray detector 2*a* of the imaging table for a recumbent position 4*a* located at the predetermined height.

Since other configurations and operations are the same as the configurations and operations of the X-ray imaging apparatus according to Embodiment 1, the description thereof will be omitted.

X-ray imaging apparatus according to Embodiment 2 is an X-ray imaging apparatus that enables the operator to freely manually cause the X-ray source 5 to travel along the rail 201 installed on the floor surface, and can capture the fluoroscopic image even in a case of the recumbent position and the standing position in a case in which a plurality of the predetermined conditions are satisfied.

EXPLANATION OF REFERENCES

1: rail
1*a*: X-ray source position for fluoroscopy

1*b*: X-ray source position for fluoroscopy
2*a*: X-ray detector
2*b*: X-ray detector
4*a*: imaging table for recumbent position
4*b*: imaging table for standing position
5: X-ray source
5*a*: irradiation field
10: subject
16: leg part
16*a*: displacement sensor
20*a*: image reception surface
20*b*: image reception surface
21: connector
21*a*: cable
22: steering wheel
23: still image capturing switch
24: fluoroscopy switch
25: X-ray console
30: X-ray high-voltage device
31: X-ray control unit
32: high-voltage generation device
33: brake
34: X-ray source position detector
40: X-ray image processing device
41: top plate
41*a*: tray position for fluoroscopy
42: tray
42*a*: mark
42*b*: handle
43: detector holding part
43*a*: mark
44: tray position sensor
44*a*: microswitch
44*b*: dog
44*c*: rail for microswitch
45: frame
46: orientation detection unit
46*a*: sensor
46*b*: sensor
47: cable connection detection unit
48: image processing unit
49: monitor
50: angle detection unit
51: X-ray source support mechanism unit
52: column part
52*a*: displacement sensor
53: mark
54: sensor
61: tray for standing position
62: detector holding part for standing position
63: leg part for standing position
101*a*: mark
101*b*: mark
150: inner rail
151: carriage
201: rail
251: column
251*a*: mark
252: arm
252*a*: mark
253: base
255: joint
256: guide groove

What is claimed is:
1. An X-ray imaging apparatus comprising:
a rail installed on a ceiling or a floor surface;
an X-ray source;
an X-ray source support mechanism unit that supports the X-ray source to be movable along the rail;
a steering wheel provided in the X-ray source support mechanism unit;
an imaging table for a standing position or for a recumbent position that holds an X-ray detector at an imaging target part of a subject;
a still image capturing switch for giving an instruction to capture a still image of the subject;
a fluoroscopy switch for giving an instruction to capture a fluoroscopic image of the subject; and
an X-ray control unit,
wherein, in a case in which one or more predetermined conditions are satisfied, the X-ray control unit permits an operation of the fluoroscopy switch, and
the predetermined conditions include a condition in which the X-ray source that is moved by an operator operating the steering wheel is stopped at a predetermined position on the rail corresponding to a position at which the X-ray detector is held.
2. The X-ray imaging apparatus according to claim 1,
wherein the rail is provided with a first mark indicating the predetermined position, and a side surface of a portion of the X-ray source support mechanism unit that is in contact with the rail is provided with a second mark as a mark, and
in a case in which the X-ray source is stopped at the predetermined position on the rail, the second mark is located at the position indicated by the first mark.
3. The X-ray imaging apparatus according to claim 1,
wherein the X-ray source support mechanism unit includes a brake that stops movement of the X-ray source by control of the X-ray control unit, and
in a case in which the operator operates the steering wheel to move the X-ray source and the X-ray source approaches the predetermined position on the rail corresponding to the position at which the X-ray detector is held, the X-ray control unit operates the brake so that the X-ray source is stopped at the predetermined position.
4. The X-ray imaging apparatus according to claim 1,
wherein the imaging table for a recumbent position includes a top plate on which the subject is placed, a tray on which the X-ray detector is placed, a detector holding part that holds the tray to be slidable along a longitudinal direction of the top plate, and a position sensor that detects whether or not the X-ray detector held by the detector holding part is located at a predetermined second position, and
the predetermined conditions in which the X-ray control unit permits the operation of the fluoroscopy switch include a condition in which the position sensor detects that the X-ray detector is located at the second position.
5. The X-ray imaging apparatus according to claim 1,
wherein the imaging table for a recumbent position includes a tray on which the X-ray detector is placed, and an orientation detection unit that detects whether or not an orientation of the X-ray detector placed on the tray is a predetermined orientation, and
the predetermined conditions in which the X-ray control unit permits the operation of the fluoroscopy switch include a condition in which the orientation detection unit detects that the X-ray detector is directed in the predetermined orientation.

6. The X-ray imaging apparatus according to claim 5, wherein the orientation detection unit includes two sensors disposed on a surface of the tray on which the X-ray detector is placed, and an interval between the two sensors is longer than a short side of the X-ray detector and shorter than a long side of the X-ray detector.

7. The X-ray imaging apparatus according to claim 1, wherein the X-ray control unit obtains a distance between the X-ray detector and the X-ray source, and the predetermined conditions in which the X-ray control unit permits the operation of the fluoroscopy switch include a condition in which the distance between the X-ray source and the X-ray detector is a predetermined distance.

8. The X-ray imaging apparatus according to claim 1, wherein the X-ray source is provided with a stop and an aperture adjustment unit that adjusts an aperture of the stop, and the predetermined conditions in which the X-ray control unit permits the operation of the fluoroscopy switch include a condition in which the aperture adjusted by the aperture adjustment unit is equal to or less than a predetermined value.

9. The X-ray imaging apparatus according to claim 1, wherein the imaging table for a standing position includes a detector holding part that holds the X-ray detector at a height desired by the operator, and a height sensor that detects the height of the X-ray detector held by the detector holding part, the X-ray source support mechanism unit includes a driving unit that adjusts a height of the X-ray source by control of the X-ray control unit, the X-ray control unit controls an operation of the driving unit so that the X-ray source is disposed at a position facing the X-ray detector in accordance with the height of the X-ray detector detected by the height sensor, and the predetermined conditions in which the X-ray control unit permits the operation of the fluoroscopy switch include a condition in which the X-ray source is disposed at the position facing the X-ray detector.

10. A control method of an X-ray imaging apparatus including a rail installed on a ceiling or a floor surface, an X-ray source, an X-ray source support mechanism unit that supports the X-ray source to be movable along the rail, a steering wheel provided in the X-ray source support mechanism unit, and an imaging table for a standing position or for a recumbent position that holds an X-ray detector at an imaging target part of a subject, the control method comprising:

continuously emitting X-rays from the X-ray source to enable fluoroscopy only in a case in which one or more predetermined conditions, including a condition in which the X-ray source is stopped at a predetermined position on the rail corresponding to a position at which the X-ray detector is held, are satisfied.

\* \* \* \* \*